July 12, 1966 M. LECOUFLE ETAL Plant Pat. 2,659
ORCHID PLANT
Filed July 30, 1965
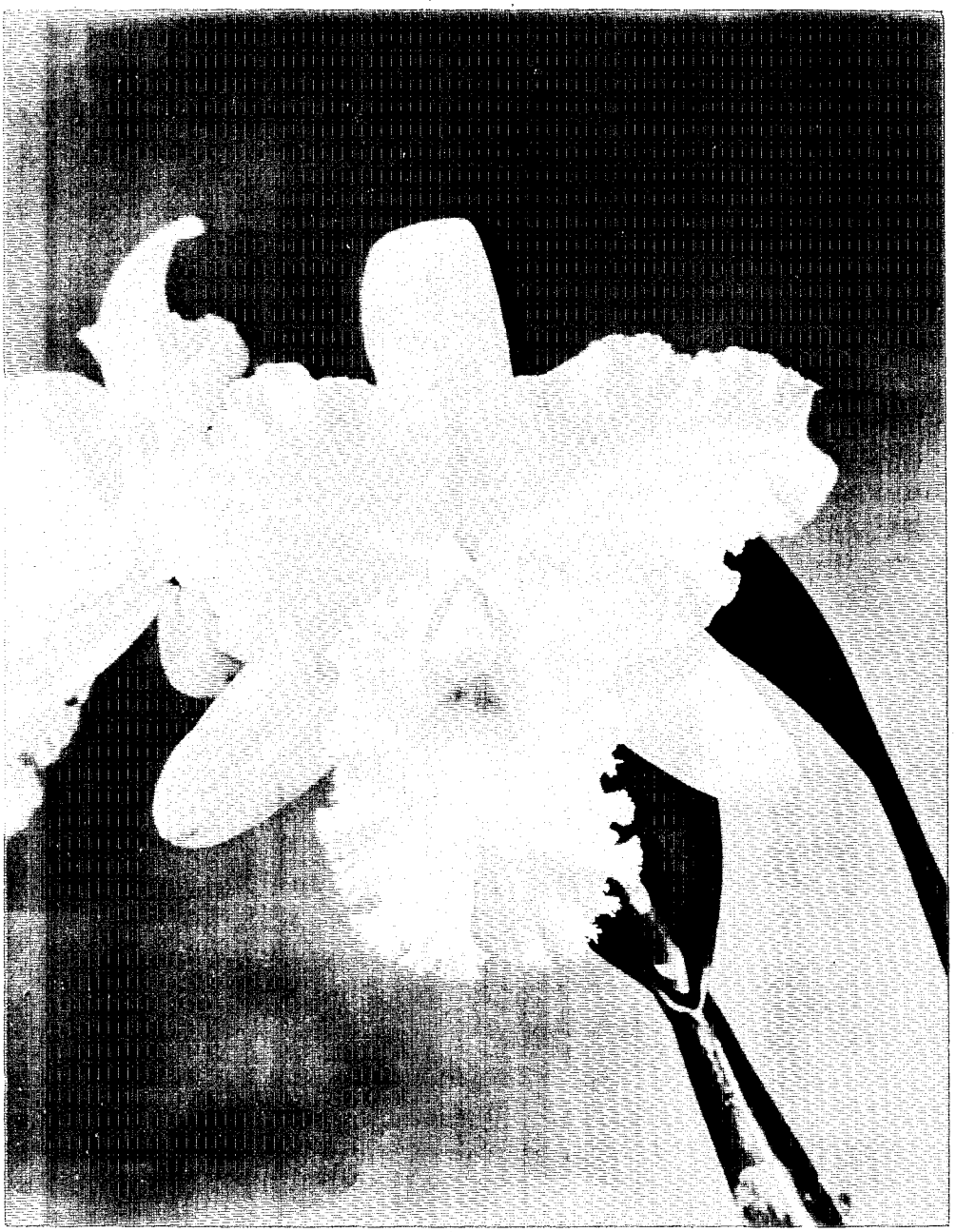
Inventors.
Maurice Lecoufle
Michel Vacherot
By: Robb & Robb
Attorneys.

United States Patent Office

Plant Pat. 2,659
Patented July 12, 1966

2,659

ORCHID PLANT

Maurice Lecoufle and Michel Vacherot, Boissy-Saint-Leger, France, assignors to Vacherot & Lecoufle, Boissy-Saint-Leger, France, a partnership

Filed July 30, 1965, Ser. No. 476,223
1 Claim. (Cl. Plt.—68)

The present invention relates to a new and distinct variety of Brassocattleya orchid plant which was originated by us as a selected seedling derived by crossing the Brassocattleya variety known as "Deesse" (unpatented) with an unnamed and unpatented variety of the species botanically known as *Cattleya Hardyana alba,* the former being the female parent and the latter being the male parent.

The primary objective of this breeding was to magnify the existing exceptional size and quality of the flowers of the parent variety Bc. "Deesse." This objective was fully achieved, along with other desirable improvements, as evidenced by the following unique combination of characteristics which are outstanding in the new variety and distinguish it from its parents, as well as from all other varieties of which we are aware:

(1) Superior strength and vigor;

(2) Clear green foliage having smooth edges;

(3) Prolific flower production, with perfectly shaped flowers usually borne in clusters of 3 flowers per cluster, and with many flowering sprouts usually growing from the same rhizome at the same time;

(4) Exceptionally large flower size, said flowers being well open and almost flat in form, and the petals being of hard substance;

(5) A distinctive and attractive pure white flower color, with Canary Yellow appearing in the interior of the labellum; and (6) An ideal suitability for commercial cut flower production, as well as for non-commercial growing by amateurs.

Asexual reproduction of our new orchid variety, as performed by us in France by meristem tissue culture (a form of botanical division), shows that the foregoing characteristics are fixed and come true and are transmissible through succeeding propagations.

The accompanying drawing shows typical specimens of the flowers and foliage of our new orchid variety as depicted in color as nearly true as it is reasonably possible to make the same in an illustration of this character.

The following is a detailed description of our new Brassocattleya orchid variety as based on observations of specimens grown by us at Boissy-Saint-Leger (Seine-et-Oise), France, with color terminology in accordance with Wilson's Horticultural Colour Chart, published in collaboration with the Royal Horticultural Society, except where general color terms of ordinary dictionary significance are obvious:

Form: Upright.

Blooming Habit: Usually bears flowers in clusters of 3 flowers per spike, with many flowering sprouts usually growing from the rhizome at the same time.

Blooming season: Autumn.

Foliage:

*Size.*—Length—about 10¼ inches. Width—about 2⅝ inches.

*Shape.*—Elliptical.

*Texture.*—Smooth.

*Edge.*—Smooth.

*Color.*—Clear green.

Bulbs:

*Length.*—About 8⅞ inches.

*Distance between bulbs.*—About 1½ inches.

*Flower*

Borne: Usually in clusters of 3 flowers per spike.

Form: Well open and almost flat. Natural spread—7¾ inches.

Petals:

*Length.*—About 3⅞ inches.

*Width.*—About 3½ inches.

Sepals:

*Length.*—About 4 inches.

*Width.*—About 1⅜ inches.

Labellum: Fringed; very long; two sides join together at the upper part, but the gymnostemium is quite visible.

*Length.*—About 3⅞ inches.

*Width.*—About 3 inches.

Color:

*Labellum.*—White, with Canary Yellow, Plate 2/1 on the interior.

*Petals and sepals.*—Pure white (one of the most white Brassocattleyas known to date and especially rare for the cut flower trade).

We claim:

A new and distinct variety of Brassocattleya orchid plant, substantially as herein shown and described, characterized particularly as to novelty by the unique combination of superior strength and vigor, clear green foliage having smooth edges, prolific flower production, with perfectly shaped flowers usually borne in clusters of 3 flowers per cluster, and with many flowering sprouts usually growing from the same rhizome at the same time, exceptionally large flower size, said flowers being well open and almost flat in form, and the petals being of hard substance, a distinctive and attractive pure white flower color, with Canary Yellow appearing in the interior of the labellum, and an ideal suitability for commercial cut flower production, as well as for non-commercial growing by amateurs.

No references cited.

ANTONIO F. GUIDA, *Acting Primary Examiner.*

R. E. BAGWILL, *Assistant Examiner.*